(12) United States Patent
Freese et al.

(10) Patent No.: US 9,013,702 B2
(45) Date of Patent: Apr. 21, 2015

(54) IMAGING SYSTEMS FOR OPTICAL COMPUTING DEVICES

(75) Inventors: Robert Freese, Pittsboro, NC (US); Christopher Michael Jones, Houston, TX (US); David Perkins, The Woodlands, TX (US); Michael Simcock, Columbia, SC (US); William Soltmann, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 378 days.

(21) Appl. No.: 13/456,467

(22) Filed: Apr. 26, 2012

(65) Prior Publication Data

US 2013/0286399 A1 Oct. 31, 2013

(51) Int. Cl.
| | |
|---|---|
| *G01N 21/00* | (2006.01) |
| *G01N 21/59* | (2006.01) |
| *G06E 3/00* | (2006.01) |
| *G01N 21/31* | (2006.01) |
| *G01N 21/85* | (2006.01) |

(52) U.S. Cl.
CPC *G01N 21/59* (2013.01); *G06E 3/00* (2013.01); *G01N 21/31* (2013.01); *G01N 21/85* (2013.01); *G06E 3/001* (2013.01); *G01N 2201/064* (2013.01)

(58) Field of Classification Search
USPC .......................................... 356/432–448, 300
See application file for complete search history.

(56) References Cited

U.S. PATENT DOCUMENTS

| | | | |
|---|---|---|---|
| 3,488,491 | A | 1/1970 | Schuman |
| 4,761,073 | A | 8/1988 | Meltz et al. |
| 4,795,262 | A | 1/1989 | Morris et al. |
| 4,806,012 | A | 2/1989 | Meltz et al. |

(Continued)

FOREIGN PATENT DOCUMENTS

| | | |
|---|---|---|
| EP | 1061355 A1 | 12/2000 |
| EP | 1969326 | 9/2008 |

(Continued)

OTHER PUBLICATIONS

Myrick et al., "Application of Multivariate Optical Computing to Simple Near-Infrared Point Measurements," Proceedings of SPIE, US, vol. 4574, 2002, pp. 208-215, XP002391230.

(Continued)

*Primary Examiner* — Tri T Ton
(74) *Attorney, Agent, or Firm* — McDermott Will & Emery LLP; Craig W. Roddy

(57) ABSTRACT

Optical computing devices are disclosed. One optical computing device includes an electromagnetic radiation source that emits electromagnetic radiation into an optical train to optically interact with a sample and at least one integrated computational element, the sample being configured to generate optically interacted radiation. A sampling window is arranged adjacent the sample and configured to allow transmission of the electromagnetic radiation therethrough and has one or more surfaces that generate one or more stray signals. A first focal lens is arranged to receive the optically interacted radiation and the one or more stray signals and generate a primary focal point from the optically interacted radiation. A structural element defines a spatial aperture aligned with the primary focal point such that the optically interacted radiation is able to pass therethrough while transmission of the one or more stray signals is substantially blocked by the structural element.

26 Claims, 4 Drawing Sheets

(56) References Cited

U.S. PATENT DOCUMENTS

| | | | |
|---|---|---|---|
| 4,882,492 A | 11/1989 | Schlager | |
| 5,399,854 A | 3/1995 | Dunphy et al. | |
| 5,426,506 A | 6/1995 | Ellingson et al. | |
| 5,493,390 A | 2/1996 | Varasi et al. | |
| 5,737,076 A | 4/1998 | Glaus et al. | |
| 6,091,504 A | 7/2000 | Walker et al. | |
| 6,198,531 B1 | 3/2001 | Myrick et al. | |
| 6,529,276 B1 | 3/2003 | Myrick | |
| 6,576,188 B1 | 6/2003 | Rose et al. | |
| 7,123,844 B2 | 10/2006 | Myrick | |
| 7,138,156 B1 | 11/2006 | Myrick et al. | |
| 7,332,094 B2 | 2/2008 | Abney et al. | |
| 7,472,748 B2 | 1/2009 | Gdanski et al. | |
| 7,623,233 B2 | 11/2009 | Freese et al. | |
| 7,697,141 B2 | 4/2010 | Jones et al. | |
| 7,712,527 B2 | 5/2010 | Roddy | |
| 7,834,999 B2 | 11/2010 | Myrick et al. | |
| 7,911,605 B2 | 3/2011 | Myrick et al. | |
| 7,920,258 B2 | 4/2011 | Myrick et al. | |
| 7,934,556 B2 | 5/2011 | Clark et al. | |
| 8,141,633 B2 | 3/2012 | Hampton et al. | |
| 8,253,619 B2 * | 8/2012 | Holbrook et al. | 342/22 |
| 8,345,234 B2 * | 1/2013 | Myrick et al. | 356/300 |
| 8,345,243 B2 | 1/2013 | Ghinovker et al. | |
| 8,547,556 B2 | 10/2013 | Irani | |
| 8,780,352 B2 | 7/2014 | Freese et al. | |
| 2001/0020675 A1 | 9/2001 | Tubel et al. | |
| 2002/0023752 A1 | 2/2002 | Qu et al. | |
| 2002/0071121 A1 | 6/2002 | Ortyn et al. | |
| 2002/0109080 A1 | 8/2002 | Tubel et al. | |
| 2003/0056581 A1 | 3/2003 | Turner et al. | |
| 2003/0145988 A1 | 8/2003 | Mullins et al. | |
| 2004/0045705 A1 | 3/2004 | Gardner et al. | |
| 2004/0129884 A1 | 7/2004 | Boyle et al. | |
| 2006/0102343 A1 | 5/2006 | Skinner et al. | |
| 2006/0142955 A1 | 6/2006 | Jones et al. | |
| 2006/0183183 A1 | 8/2006 | Felkner et al. | |
| 2007/0248488 A1 | 10/2007 | Denkewicz et al. | |
| 2007/0282647 A1 | 12/2007 | Freese et al. | |
| 2008/0041594 A1 | 2/2008 | Boles et al. | |
| 2008/0133193 A1 | 6/2008 | Gdanski et al. | |
| 2008/0231849 A1 | 9/2008 | Myrick et al. | |
| 2008/0276687 A1 | 11/2008 | Myrick et al. | |
| 2009/0002697 A1 | 1/2009 | Freese et al. | |
| 2009/0015819 A1 | 1/2009 | Van Beek et al. | |
| 2009/0033933 A1 | 2/2009 | Myrick et al. | |
| 2009/0073433 A1 | 3/2009 | Myrick et al. | |
| 2009/0087912 A1 | 4/2009 | Ramos et al. | |
| 2009/0097024 A1 | 4/2009 | Blackburn et al. | |
| 2009/0137887 A1 | 5/2009 | Shariati et al. | |
| 2009/0140144 A1 | 6/2009 | Myrick et al. | |
| 2009/0154288 A1 | 6/2009 | Heathman | |
| 2009/0182693 A1 | 7/2009 | Fulton et al. | |
| 2009/0205821 A1 | 8/2009 | Smith | |
| 2009/0213380 A1 | 8/2009 | Appel et al. | |
| 2009/0216504 A1 | 8/2009 | Priore et al. | |
| 2009/0219512 A1 | 9/2009 | Myrick et al. | |
| 2009/0219538 A1 | 9/2009 | Myrick et al. | |
| 2009/0219539 A1 | 9/2009 | Myrick et al. | |
| 2009/0250613 A1 | 10/2009 | Myrick et al. | |
| 2009/0299946 A1 | 12/2009 | Myrick et al. | |
| 2009/0305330 A1 | 12/2009 | Kroon et al. | |
| 2009/0316150 A1 | 12/2009 | Myrick et al. | |
| 2010/0006292 A1 | 1/2010 | Boles et al. | |
| 2010/0027014 A1 | 2/2010 | Hart et al. | |
| 2010/0042348 A1 | 2/2010 | Bakker | |
| 2010/0050905 A1 | 3/2010 | Lewis et al. | |
| 2010/0051266 A1 | 3/2010 | Roddy et al. | |
| 2010/0051275 A1 | 3/2010 | Lewis et al. | |
| 2010/0073666 A1 | 3/2010 | Perkins et al. | |
| 2010/0084132 A1 | 4/2010 | Noya et al. | |
| 2010/0141952 A1 | 6/2010 | Myrick et al. | |
| 2010/0148785 A1 | 6/2010 | Schaefer et al. | |
| 2010/0149523 A1 | 6/2010 | Heideman et al. | |
| 2010/0149537 A1 | 6/2010 | Myrick et al. | |
| 2010/0153048 A1 | 6/2010 | Myrick et al. | |
| 2010/0182600 A1 | 7/2010 | Freese et al. | |
| 2010/0195105 A1 | 8/2010 | Myrick et al. | |
| 2010/0245096 A1 | 9/2010 | Jones et al. | |
| 2010/0265509 A1 | 10/2010 | Jones et al. | |
| 2010/0302539 A1 | 12/2010 | Myrick et al. | |
| 2010/0305741 A1 | 12/2010 | Myrick | |
| 2010/0326659 A1 | 12/2010 | Schultz et al. | |
| 2010/0328669 A1 | 12/2010 | Myrick et al. | |
| 2011/0048708 A1 | 3/2011 | Glasbergen et al. | |
| 2011/0163046 A1 | 7/2011 | Neal et al. | |
| 2011/0199610 A1 | 8/2011 | Myrick et al. | |
| 2012/0187283 A1 | 7/2012 | Yamada et al. | |
| 2012/0211650 A1 | 8/2012 | Jones et al. | |
| 2012/0250017 A1 | 10/2012 | Morys et al. | |
| 2013/0031970 A1 | 2/2013 | Freese et al. | |
| 2013/0031971 A1 | 2/2013 | Freese et al. | |
| 2013/0031972 A1 | 2/2013 | Freese et al. | |
| 2013/0032333 A1 | 2/2013 | Freese et al. | |
| 2013/0032340 A1 | 2/2013 | Freese et al. | |
| 2013/0034842 A1 | 2/2013 | Tunheim et al. | |
| 2013/0284894 A1 | 10/2013 | Freese et al. | |
| 2013/0284895 A1 | 10/2013 | Freese et al. | |
| 2013/0284896 A1 | 10/2013 | Freese et al. | |
| 2013/0284897 A1 | 10/2013 | Freese et al. | |
| 2013/0284898 A1 | 10/2013 | Freese et al. | |
| 2013/0284899 A1 | 10/2013 | Freese et al. | |
| 2013/0284900 A1 | 10/2013 | Freese et al. | |
| 2013/0284901 A1 | 10/2013 | Freese et al. | |
| 2013/0284904 A1 | 10/2013 | Freese et al. | |
| 2013/0286398 A1 | 10/2013 | Freese et al. | |
| 2013/0287061 A1 | 10/2013 | Freese et al. | |
| 2014/0306096 A1 | 10/2014 | Freese et al. | |

FOREIGN PATENT DOCUMENTS

| | | |
|---|---|---|
| EP | 2087328 | 8/2009 |
| EP | 2140238 | 1/2010 |
| EP | 2169384 A1 | 3/2010 |
| EP | 2320027 | 5/2011 |
| GB | 2353310 A | 2/2001 |
| WO | 2004018840 A1 | 3/2004 |
| WO | 2004057285 A1 | 7/2004 |
| WO | 2005064314 A1 | 7/2005 |
| WO | 2006021928 A1 | 3/2006 |
| WO | 2006110041 A1 | 10/2006 |
| WO | 2006114773 A1 | 11/2006 |
| WO | 2006137902 | 12/2006 |
| WO | 2007064575 | 6/2007 |
| WO | 2007098392 A2 | 8/2007 |
| WO | 2008057912 A2 | 5/2008 |
| WO | 2008057913 A2 | 5/2008 |
| WO | 2011063086 A1 | 5/2011 |
| WO | 2013137744 A1 | 10/2013 |
| WO | 2013162795 A1 | 10/2013 |
| WO | 2013162799 A1 | 10/2013 |
| WO | 2013162809 A1 | 10/2013 |
| WO | 2013162860 A1 | 10/2013 |
| WO | 2013162861 A1 | 10/2013 |
| WO | 2013162901 A1 | 10/2013 |
| WO | 2013162906 A1 | 10/2013 |
| WO | 2013162913 A1 | 10/2013 |
| WO | 2013162914 A1 | 10/2013 |

OTHER PUBLICATIONS

Nelson et al., "Multivariate Optical Computation for Predictive Spectroscopy," Analytical Chemistry, vol. 70, No. 1, 1998, pp. 73-82, XP055067630.

Medendorp, et al., "Applications of Interated Sensing and Processing in Spectroscopic Imaging and Sensing," Journal of Chemometrics, vol. 19, No. 10, 2006, pp. 533-542, XP055067235.

Bin Dai et al., "Molecular Factor Computing for Predictive Spectroscopy," Pharmaceutical Research, Kluwer Academic Publishers-Plenum Publishers, NL, vol. 24, No. 8, 2007, pp. 1441-1449, XP019507244.

International Search Report and Written Opinion for PCT/US2013/036177 dated Jun. 28, 2013.

(56) References Cited

OTHER PUBLICATIONS

International Search Report and Written Opinion for PCT/US2013/036107 dated Jun. 28, 2013.
International Search Report and Written Opinion for PCT/US2013/033975 dated Jun. 28, 2013.
International Search Report and Written Opinion for PCT/US2013/035572 dated Jun. 28, 2013.
International Search Report and Written Opinion for PCT/US2013035604 dated Jun. 28, 2013.
International Search Report and Written Opinion for PCT/US2013/031467 dated Jun. 28, 2013.
International Search Report and Writen Opinion for PCT/US2013/031960 dated Jun. 28, 2013.
International Search Report and Written Opinion for PCT/US2013/032970 dated Jun. 28, 2013.
International Search Report and Written Opinion for PCT/US2013/033256 dated Jun. 28, 2013.
International Search Report and Written Opinion for PCT/US2013/033502 dated Jun. 28, 2013.
Sullivan et al. "Implementation of a Numerical Needle Method for Thin-Film Design," Applied Optics, vol. 35, No. 28, pp. 5484-5492, 1996.
Dobrowolski et al., "Refinement of Optical Multilayer Systems with Different Optimization Procedures," Applied Optics, vol. 29, No. 19, pp. 2876-2893, 1990.
Official Action for Canadian Patent Application No. 2,842,703 dated Jul. 25, 2014.
Halliburton Brochure for "Acid-on-the-Fly (AOF Blending System," published 2009.
Myrick, et al. "Spectral Tolerance Determination for Multivariate Optical Element Design," Fresenuis' Journal of Analytical Chemistry, 369:2001; pp. 351-355.
Gdanski et al., "A New Model for Matching Fracturing Fluid Flowback Composition," 2007 SPE Hydraulic Fracturing Technology Conference held in College Station, Texas, SPE 106040.
Gdanski et al., "Using Lines-of-Solutions to Understand Fracture Conductivity and Fracture Cleanup," SPE Production and Operations Symposium held in Oklahoma City, OK, 2011, SPE 142096.
Qu et al., "Fluorescence Spectral Imaging for Characterization of Tissue Based on Multivariate Statistical Analysis," Journal of the Optical Society of America, vol. 19, No. 9, 2002 XP055046065.
Bialkowski, "Species Discrimination and Quantitative Estimation Using Incoherent Linear Optical Signal Processing of Emission Signals," Analytical Chemistry, vol. 58, No. 12, 1986, pp. 2561-2563, XP055067237.
International Search Report and Written Opinion for PCT/US2013/036287 dated Aug. 2, 2013.
International Search Report and Written Opinion for PCT/US2013/036294 dated Aug. 7, 2013.

* cited by examiner

IMAGING SYSTEMS FOR OPTICAL COMPUTING DEVICES

BACKGROUND

The present invention generally relates to systems and methods of optical computing and, more specifically, to imaging systems for an optical train in an optoanalytical device.

Spectroscopic techniques for measuring various characteristics of materials are well known and are routinely used under laboratory conditions. In some cases, these spectroscopic techniques can be carried out without using an involved sample preparation. It is more common, however, to carry out various sample preparation steps before conducting the analysis. Reasons for conducting sample preparation steps can include, for example, removing interfering background materials from the analyte of interest, converting the analyte of interest into a chemical form that can be better detected by the chosen spectroscopic technique, and adding standards to improve the accuracy of quantitative measurements. Thus, there is usually a delay in obtaining an analysis due to sample preparation time, even discounting the transit time of transporting the sample to a laboratory.

Although spectroscopic techniques can, at least in principle, be conducted at a job site or in a process, the foregoing concerns regarding sample preparation times can still apply. Furthermore, the transitioning of spectroscopic instruments from a laboratory into a field or process environment can be expensive and complex. Reasons for these issues can include, for example, the need to overcome inconsistent temperature, humidity, and vibration encountered during field or process use. Furthermore, sample preparation, when required, can be difficult under field analysis conditions. The difficulty of performing sample preparation in the field can be especially problematic in the presence of interfering materials, which can further complicate conventional spectroscopic analyses. Quantitative spectroscopic measurements can be particularly challenging in both field and laboratory settings due to the need for precision and accuracy in sample preparation and spectral interpretation.

SUMMARY OF THE INVENTION

The present invention generally relates to systems and methods of optical computing and, more specifically, to imaging systems for an optical train in an optoanalytical device.

In one or more embodiments, an optical computing device is disclosed. The optical computing device may include an electromagnetic radiation source configured to emit electromagnetic radiation into an optical train, where the electromagnetic radiation optically interacts with a sample and at least one integrated computational element arranged within the optical train, the sample being configured to generate optically interacted radiation. The device may also include a sampling window arranged adjacent the sample and configured to allow transmission of the electromagnetic radiation therethrough in order to generate the optically interacted radiation into the optical train, the sampling window having one or more surfaces that generate one or more stray signals. The device may further include a first focal lens arranged to receive the optically interacted radiation and the one or more stray signals and generate a primary focal point from the optically interacted radiation, and a structural element defining a spatial aperture aligned with the primary focal point such that the optically interacted radiation is able to pass therethrough while transmission of the one or more stray signals is substantially blocked by the structural element.

In one or more embodiments, a method of operating an optical computing device is disclosed. The method may include optically interacting electromagnetic radiation with a sample and at least one integrated computational element arranged in an optical train of the optical computing device, the sample being configured to generate optically interacted radiation. The method may also include transmitting the electromagnetic radiation through a sampling window arranged adjacent the sample, the sampling window having one or more surfaces that generate one or more stray signals. The method may further include receiving and focusing the optically interacted radiation with a first focal lens and thereby generating a primary focal point, and aligning the primary focal point with a spatial aperture defined in a structural element arranged within the optical train such that the optically interacted radiation is able to pass therethrough unobstructed. The method may also include substantially blocking a transmission of the one or more stray signals with the structural element.

In at least one aspect of the disclosure, an imaging system arranged in an optical train of an optical computing device is disclosed. The imaging system may include a first focal lens arranged in the optical train and configured to receive and focus optically interacted radiation emitted from a sample and one or more stray signals emitted from a sampling window arranged adjacent the sample, the first focal lens providing a primary focal point derived from the optically interacted radiation. The imaging system may also include a structural element defining a spatial aperture aligned with the primary focal point such that the optically interacted radiation is able to pass therethrough while transmission of the one or more stray signals is blocked by the structural element, and a second focal lens arranged to receive the optically interacted radiation from the focal point and configured to convey the optically interacted radiation to at least one integrated computational element arranged in the optical train and configured to generate a modified electromagnetic radiation.

In other aspects of the disclosure, another optical computing device is disclosed. The optical computing device may include an electromagnetic radiation source configured to emit electromagnetic radiation that optically interacts with a sample arranged within an optical train, and an integrated computational element arranged in the optical train adjacent the sample and configured to allow transmission of the electromagnetic radiation therethrough in order to optically interact with the sample and thereby generate modified electromagnetic radiation, the integrated computational element having one or more surfaces that generate one or more stray signals. The device may also include a focal lens arranged in the optical train to receive the modified electromagnetic radiation and the one or more stray signals and generate a primary focal point from the modified electromagnetic radiation, and a first detector arranged at or near the primary focal point to receive the modified electromagnetic radiation from the integrated computational element, the first detector being configured to generate an output signal corresponding to a characteristic of the sample.

In yet other aspects of the disclosure, a method of operating an optical computing device is disclosed. The method may include optically interacting a sample with electromagnetic radiation transmitted through an integrated computational element arranged adjacent the sample and generating a modified electromagnetic radiation therefrom, the integrated computational element having one or more surfaces that generate one or more stray signals. The method may also include receiving and focusing the modified electromagnetic radiation with a focal lens in order to generate a primary focal point, and aligning a first detector with the primary focal point such that the modified electromagnetic radiation impinges upon the detector. The method may further include generating with the first detector an output signal corresponding to a characteristic of the sample.

The features and advantages of the present invention will be readily apparent to one having ordinary skill in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modification, alteration, and equivalents in form and function, as will occur to one having ordinary skill in the art and having the benefit of this disclosure.

DETAILED DESCRIPTION

Figure 1:
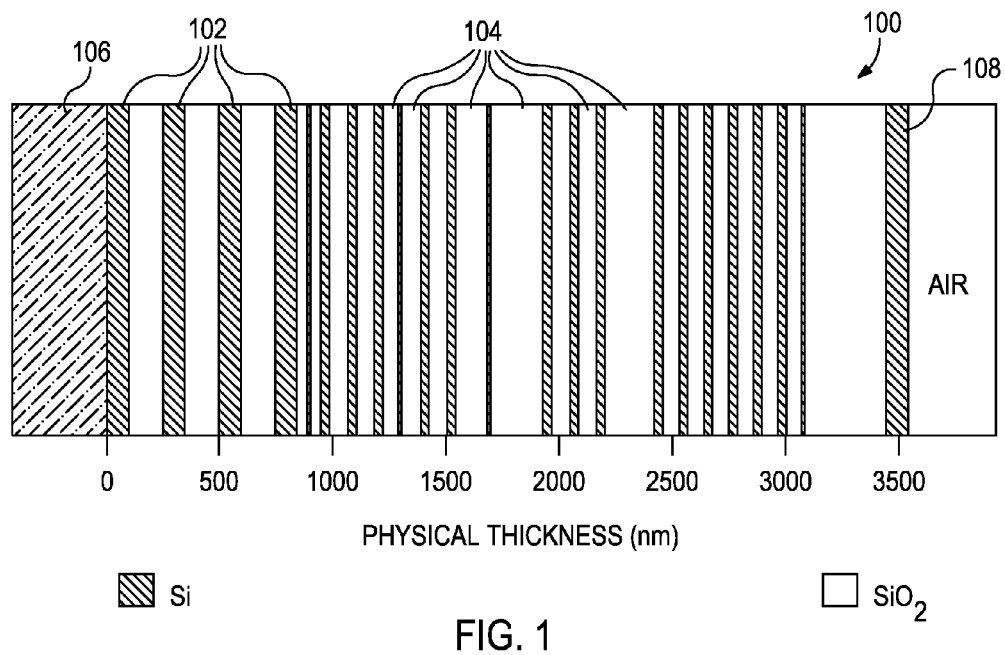
FIG. 1 illustrates an exemplary integrated computation element, according to one or more embodiments.

The present invention generally relates to systems and methods of optical computing and, more specifically, to imaging systems for an optical train in an optoanalytical device.

Embodiments described herein include various configurations of imaging systems that can be used in optical computing devices, also commonly referred to as opticoanalytical devices, in order to improve sensitivity and detection limits of the optical computing devices. The exemplary imaging systems may be suitable for use in optical computing devices as employed in the oil and gas industry. For example, optical computing devices provide a relatively low cost, rugged, and accurate system for monitoring petroleum quality for the purpose of optimizing decision making at a well site and efficient management of hydrocarbon production. In some applications, the imaging systems disclosed herein may be useful in improving detection limits when determining a particular characteristic of a substance, compound, or material present in a wellbore. It will be appreciated, however, that the exemplary imaging systems are equally applicable in optical computing devices intended to be used in other technology fields including, but not limited to, the food and drug industry, industrial applications, mining industries, or any field where it may be advantageous to determine in real-time a characteristic of a substance, compound, or material.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Fluids can include various flowable mixtures of solids, liquid and/or gases. Illustrative gases that can be considered fluids according to the present embodiments include, for example, air, nitrogen, carbon dioxide, argon, helium, hydrogen disulfide, mercaptan, thiophene, methane, ethane, butane, and other hydrocarbon gases, and/or the like.

As used herein, the term "characteristic" refers to a chemical or physical property of a substance. A characteristic of a substance may include a quantitative value of one or more chemical components therein. Such chemical components may be referred to as "analytes." Illustrative characteristics of a substance that can be monitored with the optical computing devices disclosed herein can include, for example, chemical composition (identity and concentration, in total or of individual components), impurity content, pH, viscosity, density, ionic strength, total dissolved solids, salt content, porosity, opacity, bacteria content, combinations thereof, and the like.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a substance or sample of the substance and produce an output of electromagnetic radiation from a processing element. The processing element may be, for example, an integrated computational element. The electromagnetic radiation emanating from the processing element is changed in some way so as to be readable by a detector, such that an output of the detector can be correlated to at least one characteristic of the substance. The output of electromagnetic radiation from the processing element can be reflected electromagnetic radiation, transmitted electromagnetic radiation, and/or dispersed electromagnetic radiation. As will be appreciated by those skilled in the art, whether reflected or transmitted electromagnetic radiation is analyzed by the detector will be a matter of routine experimental design. In addition, emission and/or scattering of the substance, for example via fluorescence, luminescence, radiating and re-radiating, Raman scattering, and/or Raleigh scattering can also be monitored by the optical computing devices.

As used herein, the term "optically-interact" or variations thereof refers to the reflection, transmission, scattering, diffraction, radiating, re-radiating, or absorption of electromagnetic radiation either on, through, or from one or more processing elements, such as integrated computational elements. Accordingly, optically-interacted light refers to light that has been reflected, transmitted, scattered, diffracted, or absorbed by, emitted, radiated or re-radiated, for example, using the integrated computational elements, but may also apply to interaction with a sample substance.

As used herein, the term "sample," or variations thereof, refers to at least a portion of a substance of interest to be tested or otherwise evaluated using the optical computing devices described herein. The sample includes the characteristic of interest, as defined above, and may be any fluid, as defined herein, or otherwise any solid substance or material such as, but not limited to, rock formations, concrete, other solid surfaces, etc.

The exemplary imaging systems disclosed herein may be employed in optical computing devices that include an electromagnetic radiation source, at least one processing element (e.g., an integrated computational element), and at least one detector arranged to receive optically-interacted light from the at least one processing element. The optical computing devices are specifically configured for detecting, analyzing, and quantitatively measuring a particular characteristic or analyte of interest of a given sample or substance. In some embodiments, the optical computing devices may be general purpose optical devices, with post-acquisition processing (e.g., through computer means) being used to specifically detect the characteristic of the sample.

Some suitable structural components for the optical computing devices that may employ the exemplary imaging systems disclosed herein are described in commonly owned U.S. Pat. Nos. 6,198,531; 6,529,276; 7,123,844; 7,834,999; 7,911,605, 7,920,258, and 8,049,881, each of which is incorporated herein by reference in its entirety, and U.S. patent application Ser. Nos. 12/094,460 (U.S. Pat. App. Pub. No. 2009/0219538); and 12/094,465 (U.S. Pat. App. Pub. No. 2009/0219539), each of which is also incorporated herein by reference in its entirety. As will be appreciated by those skilled in the art, variations of the structural components described in the above-referenced patents and patent applications may be suitable for use with the presently disclosed imaging systems, without departing from the scope of the disclosure.

The optical computing devices described in the foregoing patents and patent applications combine the advantage of the power, precision and accuracy associated with laboratory spectrometers, while being extremely rugged and suitable for field use. Furthermore, the optical computing devices can perform calculations (analyses) in real-time or near real-time without the need for sample processing. In this regard, the optical computing devices can be specifically configured to detect and analyze particular characteristics and/or analytes of interest. As a result, interfering signals are discriminated from those of interest in a sample by appropriate configuration of the optical computing devices, such that the optical computing devices provide a rapid response regarding the characteristics of the sample as based on the detected output. In some embodiments, the detected output can be converted into a voltage that is distinctive of the magnitude of the characteristic being monitored in the sample. The foregoing advantages and others make the optical computing devices, and their variations generally described below, particularly well suited for field and downhole use.

Optical computing devices can also be configured to detect not only the composition and concentrations of a material or mixture of materials, but they also can be configured to determine physical properties and other characteristics of the material as well, based on their analysis of the electromagnetic radiation received from the sample. For example, optical computing devices can be configured to determine the concentration of an analyte and correlate the determined concentration to a characteristic of a substance by using suitable processing means. As will be appreciated, optical computing devices may be configured to detect as many characteristics or analytes as desired in a given sample. All that is required to accomplish the monitoring of multiple characteristics or analytes is the incorporation of suitable processing and detection means within the optical computing device for each characteristic or analyte. In some embodiments, the properties of a substance or sample thereof can be a combination of the properties of the analytes therein (e.g., a linear, non-linear, logarithmic, and/or exponential combination). Accordingly, the more characteristics and analytes that are detected and analyzed using the optical computing device, the more accurately the properties of the given sample can be determined.

Fundamentally, optical computing devices utilize electromagnetic radiation to perform the required calculations, as opposed to the hardwired circuits of conventional electronic processors. When electromagnetic radiation interacts with a substance or a sample thereof, unique physical and chemical information about the substance is encoded in the electromagnetic radiation that is reflected from, transmitted through, or radiated from the sample. This information is often referred to as the spectral "fingerprint" of the substance. Optical computing devices are capable of extracting the information of the spectral fingerprint of multiple characteristics or analytes within a substance and converting that information into a detectable output regarding the overall properties of a sample. That is, through suitable configurations of the particular optical computing device, electromagnetic radiation associated with characteristics or analytes of interest in a substance can be separated from electromagnetic radiation associated with all other components of a sample in order to estimate the sample's properties in real-time or near real-time.

The processing element(s) used in the optical computing devices may be characterized as an integrated computational element (ICE). Each ICE is capable of distinguishing electromagnetic radiation related to the characteristic or analyte of interest from electromagnetic radiation related to other components of a sample substance. Referring to FIG. 1, illustrated is an exemplary ICE 100 suitable for use in the various optical computing devices described herein, according to one or more embodiments. As illustrated, the ICE 100 may include a plurality of alternating layers 102 and 104, such as silicon (Si) and $SiO_2$ (quartz), respectively. In general, these layers consist of materials whose index of refraction is high and low, respectively. Other examples might include niobia and niobium, germanium and germania, MgF, SiO, and other high and low index materials as known in the art. The layers 102, 104 may be strategically deposited on an optical substrate 106. In some embodiments, the optical substrate 106 is BK-7 optical glass. In other embodiments, the optical substrate 106 may be other types of optical substrates, such as quartz, sapphire, silicon, germanium, zinc selenide, zinc sulfide, or various plastics such as polycarbonate, polymethalmethacrylate PMMA), polyvinylchloride (PVC), diamond, ceramics, etc., as known in the art.

At the opposite end (e.g., opposite the optical substrate 106), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of the sample substance using a conventional spectroscopic instrument. The spectrum of interest of a given characteristic of a sample typically includes any number of different wavelengths. It should be understood that the exemplary ICE 100 in FIG. 1 does not in fact represent any particular characteristic of a given sample, but is provided for purposes of illustration only. Consequently, the number of layers 102, 104 and their relative thicknesses, as shown in FIG. 1, bear no correlation to any particular characteristic of a given sample. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the sample substance. For example, the layers 102, 104 may be made of, but are not limited to, silicon, germanium, water, combinations thereof, or other materials of interest.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown) which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative spacing, the exemplary ICE 100 may be configured to selectively pass/reflect/refract predetermined fractions of light (i.e., electromagnetic radiation) at different wavelengths. Each wavelength is given a predetermined weighting or loading factor. The thicknesses and spacing of the layers 102, 104 may be determined using a variety of approximation methods from the spectrograph of the character or analyte of interest. These methods may include inverse Fourier transform (IFT) of the optical transmission spectrum and structuring the ICE 100 as the physical representation of the IFT. The approximations convert the IFT into a structure based on known materials with constant refractive indices. Further information regarding the structures and design of exemplary integrated computational elements (also referred to as multivariate optical elements) is provided in *Applied Optics*, Vol. 35, pp. 5484-5492 (1996) and Vol. 129, pp. 2876-2893, which is incorporated by reference herein to the extent not inconsistent with the present disclosure.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest. Further details regarding how the exemplary ICE 100 is able to separate and process electromagnetic radiation related to the characteristic or analyte of interest are described in U.S. Pat. Nos. 6,198,531; 6,529,276; and 7,920,258, previously incorporated herein by reference.

Figure 2:
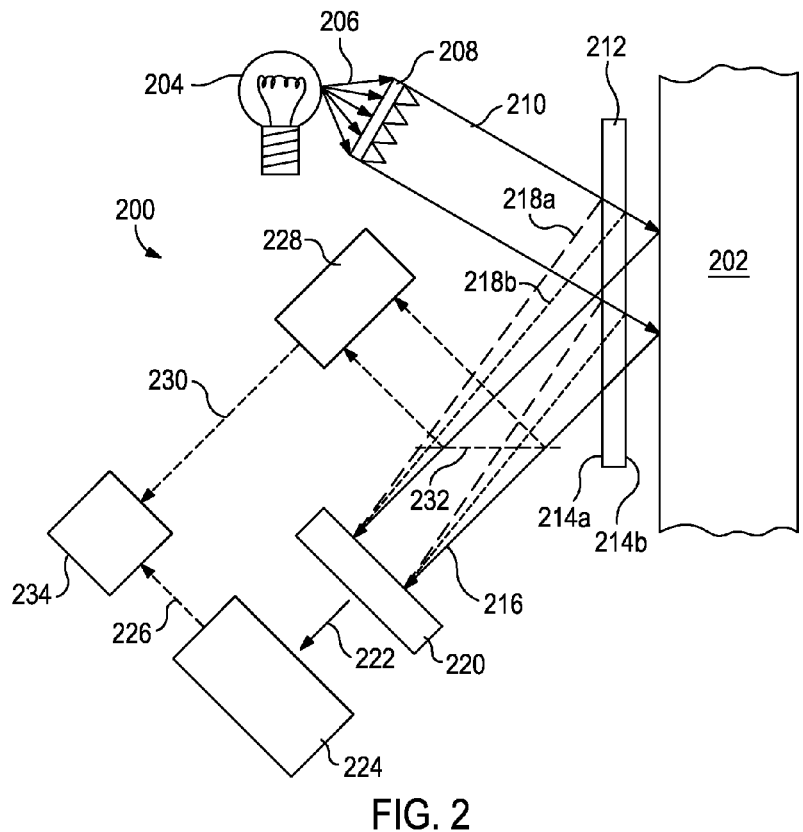
FIG. 2 illustrates an exemplary optical computing device, according to one or more embodiments.

Referring now to FIG. 2, illustrated is an optical computing device 200 useful in determining a particular characteristic of a sample 202, according to one or more embodiments. While not shown, the device 200 may be housed within a casing or housing structure configured to substantially protect the internal components of the device 200 from damage or contamination from the external environment. The sample 202 to be analyzed may be any fluid, gas, or solid that contains an analyte of interest (e.g., a characteristic) desired to be determined. In some embodiments, the sample 202 may be a mud or a concrete disposed within a wellbore and used for hydrocarbon extraction operations.

The device 200 may include an electromagnetic radiation source 204 configured to emit or otherwise generate electromagnetic radiation 206. The electromagnetic radiation source 204 may be any device capable of emitting or generating electromagnetic radiation, as defined herein. For example, the electromagnetic radiation source 204 may be a light bulb, a light emitting device (LED), a laser, a blackbody, a photonic crystal, an X-Ray source, combinations thereof, or the like. In some embodiments, a lens 208 may be configured to collect or otherwise receive the electromagnetic radiation 206 and direct a beam 210 of electromagnetic radiation 206 toward the sample 202. The lens 208 may be any type of optical device configured to transmit or otherwise convey the electromagnetic radiation 206 as desired. For example, the lens 208 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 208 may be omitted from the device 200 and the electromagnetic radiation 206 may instead be directed toward the sample 202 directly from the electromagnetic radiation source 204.

Although not specifically shown, one or more spectral elements may also be employed in the device 200 in various locations in order to restrict the optical wavelengths and/or bandwidths of the device 200 and thereby eliminate unwanted electromagnetic radiation existing in wavelength regions that have no importance. Such spectral elements can be located anywhere along the optical train, but are typically employed directly after the electromagnetic radiation source 204. Various configurations and applications of spectral elements in optical computing devices may be found in commonly owned U.S. Pat. Nos. 6,198,531; 6,529,276; 7,123,844; 7,834,999; 7,711,605, 7,920,258, 8,049,881, and U.S. patent application Ser. Nos. 12/094,460 (U.S. Pat. App. Pub. No. 2009/0219538); 12/094,465 (U.S. Pat. App. Pub. No. 2009/0219539), incorporated herein by reference to the extent not inconsistent with the current disclosure.

The device 200 may also include a sampling window 212 arranged adjacent the sample 202 for detection purposes. The sampling window 212 may be made from a variety of transparent, rigid or semi-rigid materials that are configured to allow transmission of the electromagnetic radiation 206 therethrough. For example, the sampling window 212 may be made of, but is not limited to, glasses, plastics, semi-conductors, crystalline materials, polycrystalline materials, hot or cold-pressed powders, combinations thereof, or the like. The sampling window 212 may define a first surface 214a and an opposing second surface 214b, the first surface 214a being generally exposed to the interior of the device 200 and the second surface 214b being generally exposed to the external environment surrounding the device 200 or otherwise adjacent the sample 202. It should be noted that, although FIG. 2 shows the sampling window 212 as having two parallel first and second surfaces 214a,b, it will be appreciated by those skilled in the art that one or both of these surfaces can be shaped, curved, or contain microstructures which impart optical power to the window. Thus, for example, while not shown, the sampling window 212 may consist of a lens, a grating, a holographic optical element, combinations thereof, or the like.

After passing through the sampling window 212, the beam 210 of electromagnetic radiation 206 impinges upon and optically interacts with the sample 202. As a result, optically interacted radiation 216 (e.g., sample-interacted light) is generated by and reflected from the sample 202. As the beam 210 of electromagnetic radiation 206 passes through the sampling window 212, however, the first and second surfaces 214a,b of the window 212 may also reflect or otherwise re-radiate the electromagnetic radiation 206 in the form of a first stray signal 218a and a second stray signal 218b, respectively. In alternative embodiments, it will be appreciated that the first and second stray signals 218a,b may be derived from any optical element or obstruction in the optical train. For example, in some embodiments, the window 212 may be any optical element in the optical train, without departing from the scope of the disclosure.

The optically interacted radiation 216 and each of the first and second stray signals 218a,b may be directed to or otherwise received by an ICE 220 arranged within the device 200. Since the first and second surfaces 214a,b are laterally-offset from the sample 202, it will be appreciated that the first and second stray signals 218a,b may impinge upon the ICE 220 in a manner different (e.g., at different angles or angular distributions) than that of the optically interacted radiation 216.

The ICE 220 may be an element that is substantially similar to the ICE 100 described above with reference to FIG. 1. In operation, the ICE 220 may be configured to receive the optically interacted radiation 216 and produce modified electromagnetic radiation 222 corresponding to the characteristic or analyte of interest of the sample 202. In particular, the modified electromagnetic radiation 222 may include electromagnetic radiation that has optically interacted with the ICE 220, whereby an approximate mimicking of the regression vector corresponding to the characteristic of interest of the sample 202 is obtained.

It should be noted that, while FIG. 2 depicts the ICE 220 as receiving reflected electromagnetic radiation from the sampling window 212 and the sample 202, those skilled in the art will readily recognize that the ICE 220 may be arranged at any point along the optical train of the device 200, without departing from the scope of the disclosure. For example, in one or more embodiments, the ICE 220 may be arranged before or after the lens 208 and/or prior to the sampling window 212, and equally obtain substantially the same result. In other embodiments, the sampling window 212 may serve a dual purpose as both a transmission window and the ICE 220 (i.e., a spectral element). In such cases, the detector 224 may be rearranged so as to receive the first and second stray signals 218a,b and the modified electromagnetic radiation as reflected or otherwise derived from the sample 202. Furthermore, while FIG. 2 depicts the electromagnetic radiation 206 as impinging upon and optically interacting with the sample 202 by reflection, embodiments are also contemplated herein where the electromagnetic radiation 206 is transmitted through the sample 202 and a substantially same result is obtained. Such may be the case for all of the exemplary embodiments disclosed herein.

Moreover, while only one ICE 220 is shown in FIG. 2, embodiments are contemplated herein which include the use of at least two ICE in the device 200 configured to cooperatively determine the characteristic of the sample 202. For example, two or more ICE may be arranged in series or parallel within the device 200 and configured to receive the optically interacted radiation 216 and thereby enhance sensitivities and detector limits of the device 200. In other embodiments, two or more ICE may be arranged on a movable assembly, such as a rotating disc or an oscillating linear array, which moves such that individual ICE components are able to be exposed to or otherwise optically interact with electromagnetic radiation for a distinct brief period of time. In one or more embodiments, the two or more ICE in any of these embodiments may be configured to be either associated or disassociated with the characteristic of interest of the sample 202. In other embodiments, the two or more ICE may be configured to be positively or negatively correlated with the characteristic of interest of the sample 202. These optional embodiments are further described in co-pending U.S. patent application Ser. Nos. 13/456,264, 13/456,283, and 13,456,405, filed same day herewith, the contents of which are hereby incorporated by reference in their entireties.

The modified electromagnetic radiation 222 generated by the ICE 220 may subsequently be conveyed to a detector 224 for quantification of the signal. The detector 224 may be any device capable of detecting electromagnetic radiation, and may be generally characterized as an optical transducer. For example, the detector 224 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, and/or combinations thereof, or the like, or other detectors known to those skilled in the art.

In some embodiments, the detector 224 is configured to produce an output signal 226 in the form of a voltage (or current) that corresponds to the particular characteristic of the sample 202. The voltage returned is essentially the dot product of the optical interaction of the optically interacted radiation 216 with the ICE 220 as a function of the concentration of the characteristic of interest of the sample 202. As such, the output signal 226 produced by the detector 224 and the concentration of the characteristic of the sample 202 may be related, for example, directly proportional. In other embodiments, however, the relationship may correspond to a polynomial function, an exponential function, a logarithmic function, and/or a combination thereof.

In some embodiments, the device 200 may include a second detector 228, which may be similar to the first detector 224 in that it may be any device capable of detecting electromagnetic radiation. The second detector 228 may be used to detect radiating deviations stemming from the electromagnetic radiation source 204. Undesirable radiating deviations can occur in the intensity of the electromagnetic radiation 206 due to a wide variety of reasons and potentially causing various negative effects. These negative effects can be particularly detrimental for measurements taken over a period of time. Radiating deviations can include, for example, light intensity fluctuations of the electromagnetic radiation 206. It can also include interferent fluctuations, which may scatter or absorb light from the sample 202 as it moves through the interaction space as might occur if a foreign substance such as dirt or dust is entrained within the sample 202 or otherwise passes in front of the electromagnetic radiation source 204. Radiating deviations can also include a film of material buildup on either the first or second surfaces 214a,b of the sampling window 212 which has the effect of reducing the amount and quality of light ultimately reaching the first detector 224. Without proper compensation, such radiating deviations could result in false readings and the output signal 226 would no longer be primarily or accurately related to the characteristic of interest.

To correct or compensate for these types of undesirable effects, the second detector 228 may be configured to generate a compensating signal 230 generally indicative of the radiating deviations of the electromagnetic radiation source 201, and thereby normalize the output signal 226. As illustrated, the second detector 228 may be configured to receive a portion of the optically interacted radiation 216 via a beamsplitter 232 in order to detect the radiating deviations. In other embodiments, however, the second detector 228 may be arranged to receive electromagnetic radiation from any portion of the optical train in the device 200 in order to detect the radiating deviations, without departing from the scope of the disclosure.

In some applications, the output signal 226 and the compensating signal 230 may be conveyed to or otherwise received by a signal processor 234 communicably coupled to both the detectors 224, 228. The signal processor 234 may be a computer including a non-transitory machine-readable medium, and may be configured to computationally combine the compensating signal 230 with the output signal 226 in order to normalize the output signal 226 in view of any radiating deviations detected by the second detector 228. In some embodiments, computationally combining the output and compensating signals 226, 230 may entail computing a ratio of the two signals 226, 230. For example, the concentration of each analyte or the magnitude of each characteristic determined using the optical computing device 200 can be fed into an algorithm run by the signal processor 234. The algorithm may be configured to make predictions on how the characteristics of the sample 202 change if the concentrations of the analytes are changed relative to one another. In some embodiments, the algorithm produces an output that is readable by an operator who can consider the results and make proper adjustments or take appropriate action, if needed, based upon the output.

As illustrated in FIG. 2, besides optically interacting with the optically interacted radiation 216 derived from the sample 202, the ICE 220 simultaneously receives and optically interacts with the first and second stray signals 218a,b derived from the first and second surfaces 214a,b, respectively. The light emanating from the sampling window 212 is not related to the sample 202 or its spectral fingerprint, but is instead a detrimental "ghost" image of the beam 210 of electromagnetic radiation 206. As a result, the information conveyed by the stray signals 218a,b to the ICE 220 may have a tendency to swamp or otherwise contaminate the desired signal conveyed through the optically interacted radiation 216. If not effectively reduced or otherwise prevented, the stray signals 218a,b may serve to distort the resulting modified electromagnetic radiation 222 generated by the ICE 220, resulting in substantially reduced accuracy, precision, sensitivity and limit of detection. For example, distortions include, but are not limited to, large bias voltages observed in the detector(s) 224, lower resolution in spatial images, detector saturation effects, combinations thereof, or the like.

In some embodiments, an anti-reflective (AR) coating, graded index coating, or reflection reducing microstructure may be applied to the first surface 214a or the second surface 214b of the sampling window 212, and thereby potentially eliminate a good portion of the first stray signal 218a and second stray signal 218b from propagating toward the ICE 220 and contaminating the modified electromagnetic radiation 222. In many cases, however, these mitigations alone are insufficient to reduce the contaminating signal to an acceptable level. For example, broadband AR coatings may only reduce the reflectance from 4% per surface in the case of glass, to only ½% over the spectral range of interest and therefore remain a substantial interferent or contaminant for the signal of interest (i.e., the optically interacted radiation 216). In many situations or applications, interactions of the sample 202 with the second surface 214b may prevent employment of an AR mechanism on the second surface 214b. For example, the sample 202 may chemically react with an AR coating thereby contaminating the sample 202 or compromising the effectiveness of the AR coating. In other cases, the sample 202 may abrade the AR coating or coating mechanism, particularly if the sample 202 is moving and in contact with the second surface 214b. Thus, in many applications, common AR strategies known to those skilled in the art may either not be sufficient and/or available to reduce the detrimental signals to an acceptable level. To entirely eliminate or at least reduce one or both of the first and second stray signals 218a,b, an imaging system may be included in the device 200 either without or in tandem with the AR reducing strategies discussed above.

Figure 3:
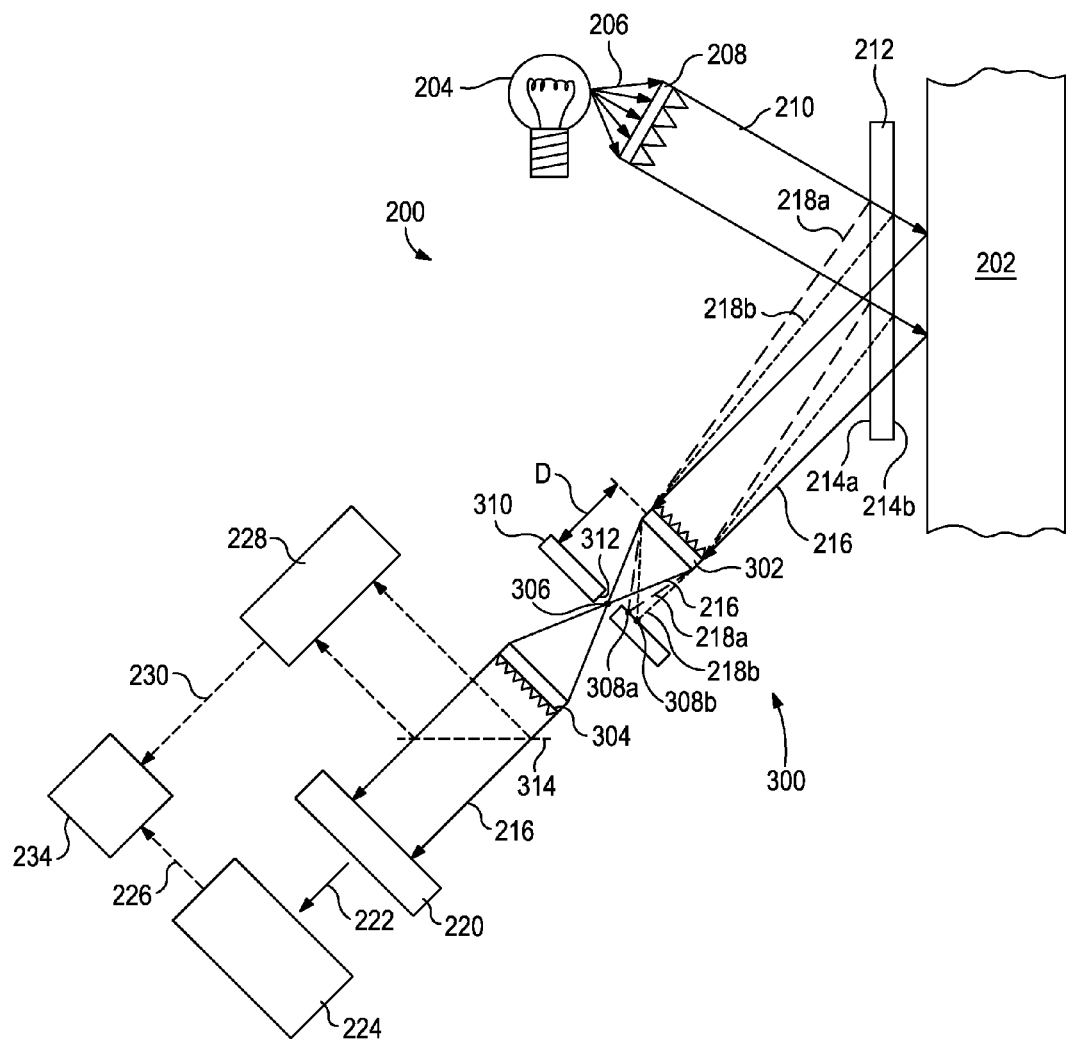
FIG. 3 illustrates an exemplary imaging system as arranged within an optical computing device, according to one or more embodiments.

Referring to FIG. 3, with continued reference to FIG. 2, illustrated is an exemplary imaging system 300 that may be used in conjunction with the optical computing device 200, according to one or more embodiments. As will be appreciated by those skilled in the art, however, the imaging system 300, and various configurations thereof, may equally be used with any optical computing device, without departing from the scope of the disclosure. The imaging system 300 may include a first focal lens 302 and a second focal lens 304. The first and second focal lenses 302, 304 may be any type of optical device configured to transmit or otherwise convey electromagnetic radiation as desired. For example, the focal lenses 302, 304 may be normal lenses, Fresnel lenses, diffractive optical elements, holographic graphical elements, mirrors (e.g., a focusing mirror), digital light pipe, gradient index (GRIN) lenses, or any type of collimator known to those skilled in art.

As illustrated, the first focal lens 302 may be configured to receive and focus the optically interacted radiation 216 to a primary focal point 306. The primary focal point 306 may be defined in the optical train at a focal distance D from the first focal lens 302, at which point the optically interacted radiation 216 diverges once again toward the second focal lens 304. As will be appreciated, the focal distance D may be varied depending on the particular design of the first focal lens 302. Accordingly, those skilled in the art will readily recognize that the various parameters and sizes of the imaging system 300 may be altered by using alternatively designed components, such as alternative configurations of the first focal lens 302.

The second focal lens 304 may be configured to receive and collimate the optically interacted radiation 216 and convey the same toward the ICE 220. In at least one embodiment, however, the second focal lens 304 may be omitted from the imaging system 300 and the ICE 220 may instead be arranged to receive the diverging optically interacted radiation 216.

In some embodiments, the first focal lens 302 may also be configured to receive and focus the first and second stray signals 218a,b to a first stray focal point 308a and a second stray focal point 308b, respectively. However, since the first and second stray signals 218a,b are conveyed toward the first focal lens 302 at an angle at least slightly offset from the angle at which the optically interacted radiation 216 is conveyed thereto, the respective focal points 308a,b will also be at least slightly offset from the primary focal point 306. In other embodiments, however, the first focal lens 302 may not necessarily need to focus the first and second stray signals 218a,b to the respective first and second stray focal points 308a,b. Instead, the first and second stray signals 218a,b may simply impinge upon the first focal lens 302 which otherwise directs any transmissive beams of electromagnetic radiation derived from the first and second stray signals 218a,b away from the general location of the primary focal point 306.

In order to remove the unwanted stray signals 218a,b from the device 200, and thereby generally prevent the contamination and distortion of the resulting modified electromagnetic radiation 222, the imaging system 300 may further include a structural element 310. As depicted, the structural element 310 may generally interpose the first and second focal lenses 302, 304 and have a spatial aperture 312 defined therein. In some embodiments, the structural element 310 may be a monolithic member that defines the spatial aperture 312. In other embodiments, however, the structural element 310 may provide two or more component portions that cooperatively define the spatial aperture 312.

The structural element 310 may be arranged at about the focal distance D such that the spatial aperture 312 coincides with or otherwise receives the primary focal point 306 while simultaneously blocking the first and second stray focal points 308a,b. Specifically, the spatial aperture 312 may be aligned with the primary focal point 306 such that the optically interacted radiation 216 is able to pass through the structural element 310 unobstructed at the primary focal point 306, while the first and second stray signals 218a,b are blocked or otherwise absorbed by the structural element 310. As a result, only the optically interacted radiation 216 is conveyed to the ICE 220 and the unwanted first and second stray signals 218a,b are therefore unable to contaminate the resulting modified electromagnetic radiation 222. Consequently, the output signal 226 may more accurately reflect the characteristic of interest of the sample 202.

In other embodiments, however, a reflective device (not shown), such as a mirror or the like, may be arranged at or near the spatial aperture 312 and configured to redirect the optically interacted radiation toward the detector 224 while the structural element 310 generally blocks the first and second stray signals 218a,b. In yet other embodiments, the structural element 310 may be omitted altogether and the exemplary reflective device (not shown) may be arranged at or near the primary focal point 306 in order to redirect the optically interacted radiation toward the detector 224.

As with the embodiment shown in FIG. 2, the device 200 may include the second detector 228 used to detect radiating deviations stemming from the electromagnetic radiation source 204. As illustrated, the second detector 228 may be configured to receive a portion of the optically interacted radiation 216 via a beamsplitter 314 arranged after the second focal lens 304. In other embodiments, however, the second detector 228 may be arranged to receive electromagnetic radiation from any portion of the optical train in the device 200 in order to detect the radiating deviations, without departing from the scope of the disclosure. For example, a light pipe, such as an optical fiber or bundle of fibers (not shown), may be used to transfer the electromagnetic radiation from the primary focal point 306 directly to one or both of the second detector 228 and the ICE 220. Moreover, those knowledgeable in the art will also appreciate that electromagnetic radiation can be conveyed directly from the source 204 and/or the sample 202 via elements other than lenses and mirrors, such as, but not limited to, light pipes, optical fibers (either single or multi-mode), bundles of optical fibers, diffraction gratings, digital light pipes (DLP), scanners, and the like. Again, the output signal 226 and the compensating signal 230 may be conveyed to or otherwise received by the signal processor 234 which may be configured to computationally combine the compensating signal 230 with the output signal 226 in order to normalize the output signal 226 in view of any radiating deviations detected by the second detector 228.

Figure 4:
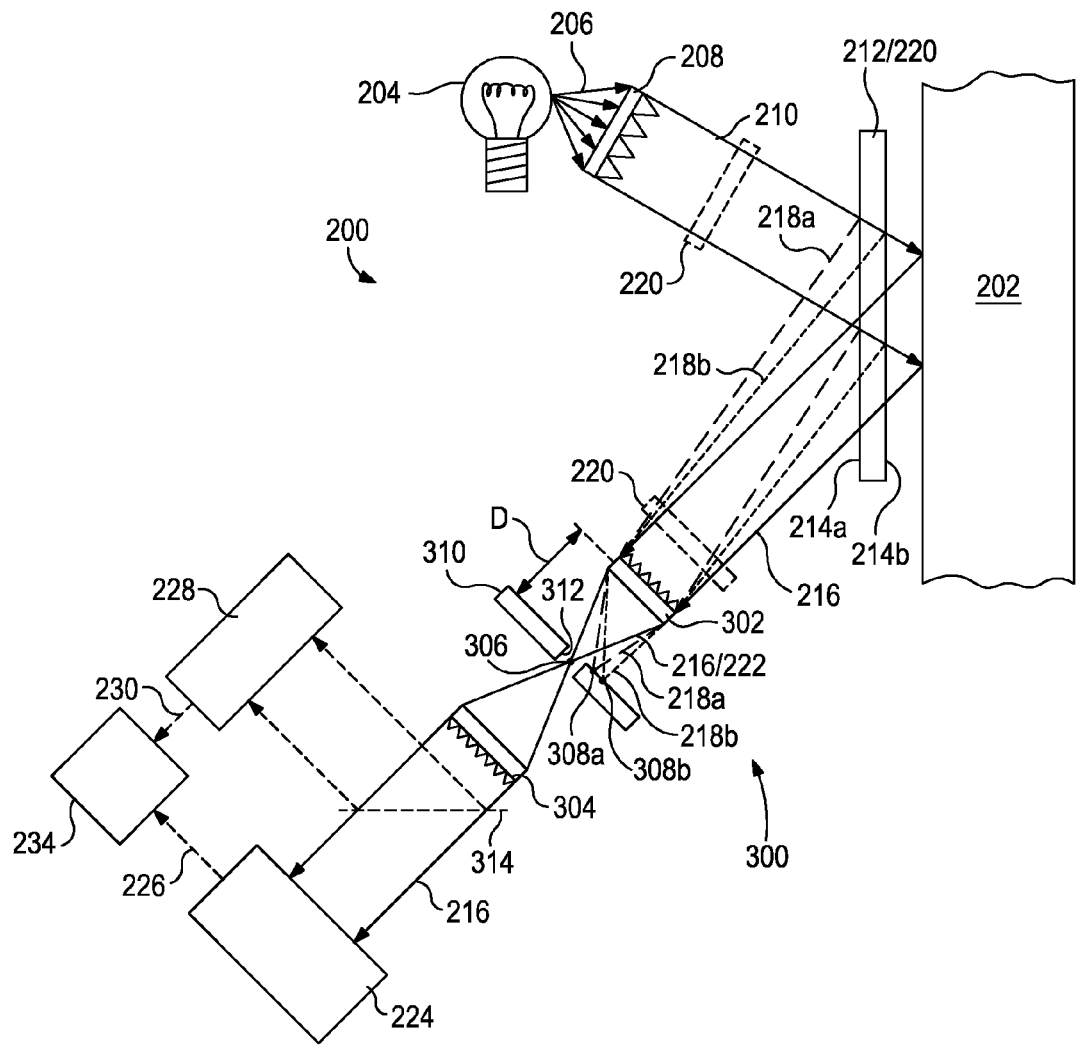
FIG. 4 illustrates another exemplary imaging system as arranged within an optical computing device, according to one or more embodiments.

Referring now to FIG. 4, illustrated is another exemplary imaging system 400 that may be used in conjunction with the optical computing device 200, according to one or more embodiments. The imaging system 400 may be similar in some respects to the imaging system 300 of FIG. 3, and therefore may be best understood with reference thereto, where like numerals represent like components that will not be described again in detail. In FIG. 4, the ICE 220 is shown as being optionally placed or otherwise arranged at several locations along the optical train of the device 200. For instance, the ICE 220 may be arranged after the lens 208 but prior to the sampling window 212. In such an embodiment, the beam 210 of electromagnetic radiation 206 may impinge upon the ICE 220 and the modified electromagnetic radiation 220 (not shown) may be generated therefrom and conveyed to the sample 202 to optically interact therewith.

In other embodiments, as illustrated, the ICE 220 may alternatively be arranged after the sampling window 212 in the optical train of the device 200, but before the first focal lens 302. As a result, the optically interacted radiation 216 that emanates from the sample 202 may impinge upon the ICE 220 and the modified electromagnetic radiation 220 (not shown) may be generated therefrom and subsequently conveyed to first focal lens 302. In yet other embodiments, the sampling window 212 may serve a dual purpose as the sampling window 212 and the ICE 220 such that the optically interacted radiation 216 reflected from the sample 202 may simultaneously be configured or otherwise conveyed as the modified electromagnetic radiation 222 having been optically interacted with both the sample 202 and the ICE 220. It should be noted that, while FIG. 4 depicts the electromagnetic radiation as being transmitted through each exemplary arrangement of the ICE 220, embodiments are contemplated herein where the ICE 220 reflects the electromagnetic radiation, without departing from the scope of the disclosure.

Similar to the imaging system 300 of FIG. 3, the first focal lens 302 may be configured to receive and focus the optically interacted radiation 216 (combined with the modified electromagnetic radiation 220) to the primary focal point 306 defined in the optical train at a focal distance D from the first focal lens 302. In some embodiments, the first focal lens 302 may also receive and focus the first and second stray signals 218a,b to the first stray focal point 308a and the second stray focal point 308b, respectively. In other embodiments, however, the first and second stray signals 218a,b may simply impinge upon the first focal lens 302 which otherwise directs any transmissive beams of electromagnetic radiation derived from the first and second stray signals 218a,b away from the general location of the primary focal point 306.

As illustrated, the second focal lens 304 may be configured to receive the diverging beam of optically interacted radiation 216 (combined with the modified electromagnetic radiation 220) and direct the same to the first detector 224 in order to generate the output signal 226 corresponding to the characteristic of the sample 202. In other embodiments, the first detector 224 may be arranged to directly receive the diverging beam of optically interacted radiation 216 (combined with the modified electromagnetic radiation 220), without departing from the scope of the disclosure. Moreover, the device 200 may again include the second detector 228 used to detect radiating deviations. As illustrated, the second detector 228 may be configured to receive a portion of the optically interacted radiation 216 via the beamsplitter 314 arranged after the second focal lens 304. In other embodiments, however, the second detector 228 may be arranged to receive electromagnetic radiation from any portion of the optical train in the device 200 in order to detect the radiating deviations, without departing from the scope of the disclosure. Again, the output signal 226 and the compensating signal 230 may be conveyed to or otherwise received by the signal processor 234 which may be configured to computationally combine the compensating signal 230 with the output signal 226 in order to normalize the output signal 226 in view of any radiating deviations detected by the second detector 228.

Figure 5:
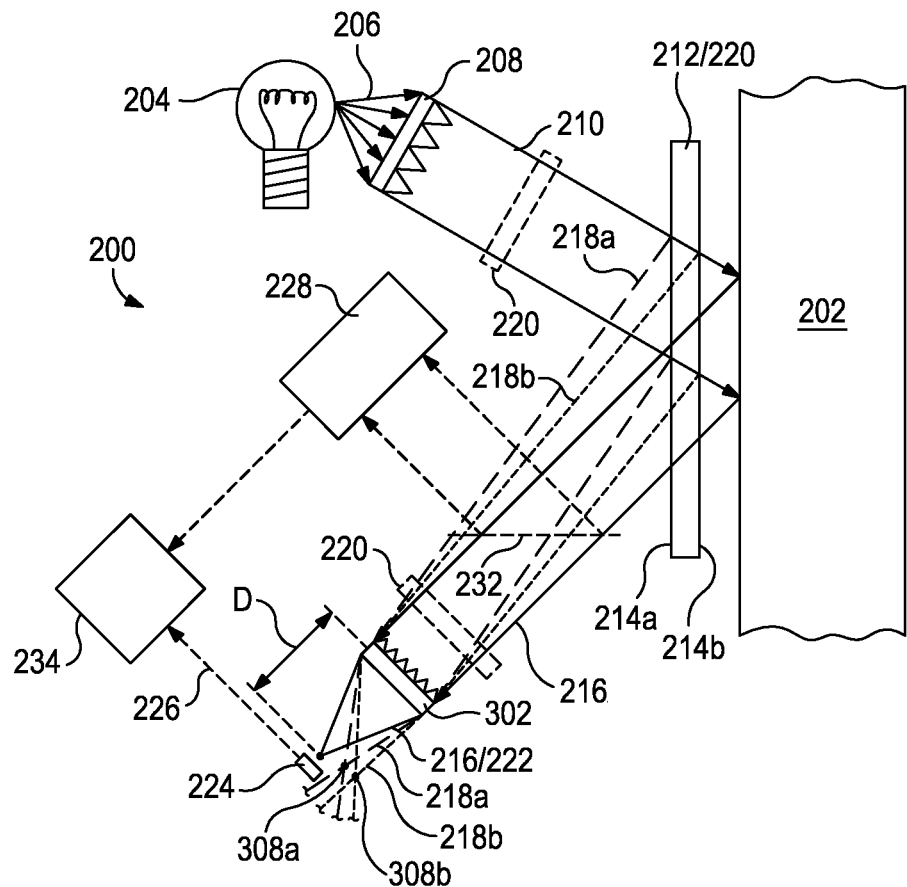
FIG. 5 illustrates another exemplary imaging system as arranged within an optical computing device, according to one or more embodiments.

Referring now to FIG. 5, illustrated is another exemplary imaging system 500 that may be used in conjunction with the optical computing device 200, according to one or more embodiments. The imaging system 500 may be similar in some respects to the imaging systems 300 and 400 of FIGS. 3 and 4, respectively, and therefore may be best understood with reference thereto, where like numerals represent like components that will not be described again in detail. Similar to the embodiments illustrated in FIG. 4, the ICE 220 in FIG. 5 is shown as being optionally placed or otherwise arranged at several locations along the optical train of the device 200. For example, the ICE 220 may again be arranged after the lens 208 but prior to the sampling window 212, after the sampling window 212 but before the first focal lens 302, and/or the sampling window 212 itself may be a spectral element (i.e., the ICE 220). Moreover, it is again noted that, while FIG. 5 depicts the electromagnetic radiation as being transmitted through each exemplary arrangement of the ICE 220, embodiments are contemplated herein where the ICE 220 reflects the electromagnetic radiation, without departing from the scope of the disclosure.

Similar to the imaging systems 300 and 400 of FIGS. 3 and 4, the first focal lens 302 configured to receive and focus the optically interacted radiation 216 (combined with the modified electromagnetic radiation 220) to the primary focal point 306 defined in the optical train at a focal distance D from the first focal lens 302. The first focal lens 302 may also receive and focus the first and second stray signals 218$a,b$ to the first stray focal point 308$a$ and the second stray focal point 308$b$, respectively.

The first focal lens 302 may again be configured to receive and focus the optically interacted radiation 216 (combined with the modified electromagnetic radiation 220) to the primary focal point 306 defined in the optical train at a focal distance D from the first focal lens 302. In some embodiments, the first focal lens 302 may also receive and focus the first and second stray signals 218$a,b$ to the first and second stray focal points 308$a,b$, respectively. In other embodiments, however, the first and second stray signals 218$a,b$ may simply impinge upon the first focal lens 302 which otherwise directs any transmissive beams of electromagnetic radiation derived from the first and second stray signals 218$a,b$ away from the general location of the primary focal point 306.

In order to remove the unwanted stray signals 218$a,b$ from the device 200, and thereby generally prevent the contamination and distortion of the resulting output signal 226, the first detector 224 may be sized and arranged so as to only receive the optically interacted radiation 216 at or near the primary focal point 306. In other embodiments, the first detector 224 may be sized or otherwise arranged within the aperture 312 of the imaging system 300 of FIG. 3, and obtain the same result. Because of the reduced size of the first detector 224 and the offset first and second stray focal points 308$a,b$, the first and second stray signals 218$a,b$ will be conveyed past the first detector 224 or otherwise be unable to impinge thereupon. As a result, the output signal 226 from the first detector 224 may more accurately reflect the characteristic of interest of the sample 202.

Those skilled in the art will readily appreciate that the electromagnetic radiation that interacts with the sample 202 may be collected or otherwise detected in a transmissive mode instead of the reflective mode generally shown in FIGS. 2-5. In the transmissive mode, for example, the unwanted stray signals (e.g., signals 218$a,b$) may emanate from windows or spectral elements located on either side of the sample 202, but may nonetheless be removed or otherwise attenuated using the generally methods described herein. Moreover, it will also be appreciated by those skilled in the art that besides the stray signals 218$a,b$ emanating from the surfaces 214$a,b$ of the window 212, one or more additional stray signals could also be generated from other optical elements or obstructions found in the optical train. For example, one or more additional unwanted stray signals may also be generated from various enclosure or enclosure walls. This may be especially applicable where the electromagnetic radiation is infrared, or the like.

While the various embodiments disclosed herein provide that the electromagnetic radiation source 204 is used to provide electromagnetic radiation that optically interacts with the sample 202, those skilled in the art will readily recognize that electromagnetic radiation may be derived directly from the sample 202 itself, and otherwise derived independent of the electromagnetic radiation source 201. For example, various substances naturally radiate electromagnetic radiation that is able to optically interact with the ICE component. In some embodiments, the sample 202 may be a blackbody radiating substance configured to radiate heat that may optically interact with the ICE component. In other embodiments, the sample 202 may be radioactive or chemo-luminescent and therefore radiate electromagnetic radiation that is able to optically interact with the ICE component. In yet other embodiments, the electromagnetic radiation may be induced from the sample 202 by being acted upon mechanically, magnetically, electrically, combinations thereof, or the like. For instance, in at least one embodiment a voltage may be placed across the sample 202 in order to induce the electromagnetic radiation. As a result, embodiments are contemplated herein where the electromagnetic radiation source 204 is entirely omitted from the particular optical computing device, and the one or more unwanted stray signals (e.g., signals 218$a,b$) may nonetheless emanate from a variety of optical elements or obstructions in the optical train.

It should also be noted that the various drawings provided herein are not necessarily drawn to scale nor are they, strictly speaking, depicted as optically correct as understood by those skilled in the art. Instead, the drawings are merely illustrative in nature and used generally herein in order to supplement understanding of the description provided above. Indeed, while the drawings may not be optically accurate, the conceptual interpretations depicted therein accurately reflect the exemplary nature of the various embodiments disclosed.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. An optical computing device, comprising:
an electromagnetic radiation source that emits electromagnetic radiation into an optical train to optically interact with a sample and at least one integrated computational element arranged within the optical train, the sample generating optically interacted radiation upon optically interacting with the electromagnetic radiation;
a sampling window arranged adjacent the sample and allowing transmission of the electromagnetic radiation therethrough in order to generate the optically interacted radiation, the sampling window having one or more surfaces that generate one or more stray signals;
a first focal lens arranged to receive the optically interacted radiation and the one or more stray signals and generate a primary focal point from the optically interacted radiation; and
a structural element defining a spatial aperture aligned with the primary focal point such that the optically interacted radiation is able to pass therethrough while transmission of the one or more stray signals is substantially blocked by the structural element.

2. The device of claim 1, wherein the at least one integrated computational element is arranged in the optical train before the sampling window.

3. The device of claim 1, wherein the at least one integrated computational element is arranged in the optical train after the sampling window and before the first focal lens.

4. The device of claim 1, further comprising a detector arranged at or near the primary focal point to receive modified electromagnetic radiation emitted from the integrated computational element, the first detector being configured to generate an output signal corresponding to a characteristic of the sample.

5. The device of claim 4, wherein the detector is arranged in the spatial aperture.

6. The device of claim 1, further comprising a reflective device arranged at or near the primary focal point to receive modified electromagnetic radiation emitted from the integrated computational element, the reflective device being configured to reflect the modified electromagnetic radiation toward a detector which generates an output signal corresponding to a characteristic of the sample.

7. The device of claim 1, wherein the sample is one of a fluid, a gas, a powder, or a solid.

8. The device of claim 7, wherein the sample is a mud or a concrete disposed within a wellbore.

9. The device of claim 1, wherein the electromagnetic radiation is transmitted through the sample to generate the optically interacted radiation.

10. The device of claim 1, wherein the electromagnetic radiation is reflected off of the sample to generate the optically interacted radiation.

11. The device of claim 1, further comprising a lens configured to receive the electromagnetic radiation and direct a beam of electromagnetic radiation toward the sample.

12. The device of claim 1, wherein the optically interacted radiation and the one or more stray signals are received by the first focal lens at different angles.

13. The device of claim 1, wherein the integrated computational element is arranged to receive the optically interacted radiation from a second focal lens arranged to receive the optically interacted radiation from the focal point, the at least one integrated computational element being configured to generate a modified electromagnetic radiation.

14. The device of claim 13, further comprising a first detector arranged to receive the modified electromagnetic radiation from the at least one integrated computational element and thereby generate an output signal corresponding to a characteristic of the sample.

15. The device of claim 14, further comprising:
a second detector arranged to receive and detect at least a portion of the optically interacted radiation from the second focal lens, the second detector being configured to generate a compensating signal indicative of radiating deviations of the electromagnetic radiation source; and
a signal processor communicably coupled to the first and second detectors and configured to receive and computationally combine the output signal and the compensating signal in order to determine the characteristic of the sample.

16. The device of claim 1, further comprising one or more additional stray signals being generated by additional optical elements or obstructions found in the optical train, the structural element being configured to also substantially block transmission of the one or more additional stray signals.

17. The device of claim 1, wherein the at least one integrated computational element is arranged to receive the optically interacted radiation from the primary focal point and generate a modified electromagnetic radiation, the device further comprising a first detector arranged to receive the modified electromagnetic radiation from the at least one integrated computational element and thereby generate an output signal corresponding to a characteristic of the sample.

18. An imaging system arranged in an optical train of an optical computing device, comprising:
a first focal lens arranged in the optical train and configured to receive and focus optically interacted radiation emitted from a sample and one or more stray signals emitted from a sampling window arranged adjacent the sample, the first focal lens providing a primary focal point derived from the optically interacted radiation;
a structural element defining a spatial aperture aligned with the primary focal point such that the optically interacted radiation is able to pass therethrough while transmission of the one or more stray signals is blocked by the structural element; and
a second focal lens arranged to receive the optically interacted radiation from the focal point and configured to convey the optically interacted radiation to at least one integrated computational element arranged in the optical train and configured to generate a modified electromagnetic radiation.

19. The imaging system of claim 18, wherein the optically interacted radiation and the one or more stray signals are received by the first focal lens at different angles.

20. The imaging system of claim 18, wherein the structural element is monolithic.

21. The imaging system of claim 18, wherein the structural element is made of two or more component portions that cooperatively define the spatial aperture.

22. An optical computing device, comprising:
an electromagnetic radiation source that emits electromagnetic radiation that optically interacts with a sample arranged within an optical train;
an integrated computational element arranged in the optical train adjacent the sample and allowing transmission of the electromagnetic radiation therethrough to optically interact with the sample and thereby generate modified electromagnetic radiation, the integrated computational element having one or more surfaces that generate one or more stray signals;

a focal lens arranged in the optical train to receive the modified electromagnetic radiation and the one or more stray signals and generate a primary focal point from the modified electromagnetic radiation; and a first detector arranged at or near the primary focal point to receive the modified electromagnetic radiation from the integrated computational element, the first detector generating an output signal corresponding to a characteristic of the sample.

23. The device of claim 22, wherein the sample is one of a fluid, a gas, a powder, or a solid.

24. The device of claim 23, wherein the sample is a mud or a concrete disposed within a wellbore.

25. The device of claim 22, wherein the modified electromagnetic radiation and the one or more stray signals are received by the first focal lens at different angles.

26. The device of claim 22, further comprising:

a second detector arranged to receive and detect at least a portion of the modified electromagnetic radiation and generate a compensating signal indicative of radiating deviations of the electromagnetic radiation source; and a signal processor communicably coupled to the first and second detectors and configured to receive and computationally combine the output signal and the compensating signal in order to determine the characteristic of the sample.

* * * * *